(12) United States Patent
Anderson et al.

(10) Patent No.: US 8,460,354 B2
(45) Date of Patent: Jun. 11, 2013

(54) INFLATABLE CONVECTIVE PAD FOR SURGERY

(75) Inventors: Thomas P. Anderson, Savage, MN (US); Mark J. Scott, Maple Grove, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

(21) Appl. No.: 12/925,249

(22) Filed: Oct. 15, 2010

(65) Prior Publication Data

US 2011/0098794 A1   Apr. 28, 2011

Related U.S. Application Data

(62) Division of application No. 10/935,992, filed on Sep. 8, 2004.

(51) Int. Cl.
  *A61F 7/02* (2006.01)
(52) U.S. Cl.
  CPC ........................................ *A61F 7/02* (2013.01)
  USPC ....................................................... 607/108
(58) Field of Classification Search
  USPC .................................. 607/104–112; 128/898
  See application file for complete search history.

(56) References Cited

U.S. PATENT DOCUMENTS

| | | | |
|---|---|---|---|
| 2,930,594 A | 3/1960 | MacCracken | 607/104 |
| 3,089,153 A | 5/1963 | Bosc | 5/348 |
| 3,674,019 A | 7/1972 | Grant | 601/148 |
| 3,778,851 A | 12/1973 | Howorth | 5/347 |
| 3,867,939 A | 2/1975 | Moore et al. | 604/291 |
| 4,005,236 A | 1/1977 | Graebe | 428/72 |
| 4,091,808 A | 5/1978 | Nelson | 128/133 |
| 4,114,620 A | 9/1978 | Moore et al. | 128/254 |
| 4,541,136 A | 9/1985 | Graebe | 5/456 |
| 4,867,230 A | 9/1989 | Voss | 165/46 |
| 5,022,110 A | 6/1991 | Stroh | 5/455 |
| 5,033,136 A | 7/1991 | Elkins | 5/421 |
| 5,165,400 A | 11/1992 | Berke | 128/400 |
| 5,184,612 A | 2/1993 | Augustine | 128/400 |
| 5,265,599 A | 11/1993 | Stephenson et al. | 607/104 |
| 5,300,102 A | 4/1994 | Augustine et al. | 607/107 |
| 5,304,213 A | 4/1994 | Berke et al. | 607/104 |

(Continued)

FOREIGN PATENT DOCUMENTS

| | | |
|---|---|---|
| DE | 3320771 A1 | 12/1984 |
| EP | 0757907 A1 | 2/1997 |

(Continued)

OTHER PUBLICATIONS

IPER for PCT/US99/12622, mailed Oct. 25, 2000.

(Continued)

*Primary Examiner* — Aaron Roane
(74) *Attorney, Agent, or Firm* — X. Christina Huang; Adam M. Brammwell; Terrance A. Meador

(57) ABSTRACT

An inflatable convective pad for warming a person during surgery has two ends, two sides, and at least two openings, each located in an area of the pad between the two ends and between a respective side and the center of the pad. The openings, which may be in the form of slits, allow the threading of a sheet or the person's arms through the pad to restrain the arms during surgery.

4 Claims, 10 Drawing Sheets

U.S. PATENT DOCUMENTS

| | | | |
|---|---|---|---|
| 5,336,250 A | 8/1994 | Augustine | 607/107 |
| 5,342,290 A * | 8/1994 | Schuellein | 602/36 |
| 5,370,605 A * | 12/1994 | Weed | 602/35 |
| 5,383,476 A * | 1/1995 | Peimer et al. | 128/849 |
| 5,561,875 A | 10/1996 | Graebe | 5/423 |
| 5,603,690 A | 2/1997 | Barry | 601/148 |
| 5,620,482 A | 4/1997 | Augustine et al. | 607/107 |
| 5,640,727 A | 6/1997 | Kappel | 5/482 |
| 5,640,728 A | 6/1997 | Graebe | 5/606 |
| 5,655,237 A | 8/1997 | Suzuki et al. | 5/502 |
| 5,683,441 A | 11/1997 | Dickerhoff et al. | 607/107 |
| 5,702,375 A | 12/1997 | Angelillo et al. | 604/358 |
| 5,735,890 A | 4/1998 | Kappel et al. | 607/104 |
| 5,785,716 A | 7/1998 | Bayron et al. | 607/108 |
| 5,800,489 A | 9/1998 | Augustine | 607/107 |
| 5,860,292 A | 1/1999 | Augustine et al. | 62/259.3 |
| 5,891,187 A | 4/1999 | Winthrop et al. | 607/96 |
| 5,941,907 A | 8/1999 | Augustine | 607/104 |
| 5,989,285 A | 11/1999 | deVilbiss et al. | 607/107 |
| 5,997,572 A | 12/1999 | Arnold et al. | 604/104 |
| 6,102,936 A | 8/2000 | Augustine et al. | 607/96 |
| 6,119,474 A | 9/2000 | Augustine et al. | 62/259.3 |
| 6,511,501 B1 | 1/2003 | Augustine et al. | 607/96 |
| 6,859,939 B1 | 3/2005 | Osburn, Sr. | 2/69 |
| 7,172,616 B2 | 2/2007 | Schuessler et al. | 607/107 |
| 7,591,029 B2 | 9/2009 | Weedling et al. | 5/81.1 |
| 2005/0143797 A1 | 6/2005 | Parish et al. | 607/104 |
| 2006/0052851 A1 | 3/2006 | Anderson et al. | 607/104 |
| 2006/0161231 A1 | 7/2006 | Cazzini et al. | 607/104 |
| 2007/0244533 A1 | 10/2007 | Pierre et al. | 607/107 |
| 2009/0248120 A1 | 10/2009 | Starr et al. | 606/107 |
| 2011/0009930 A1 | 1/2011 | Officier et al. | 607/104 |

FOREIGN PATENT DOCUMENTS

| | | |
|---|---|---|
| EP | 1096907 | 3/2006 |
| GB | 1350110 | 4/1974 |
| GB | 2228193 A | 8/1990 |
| WO | WO 00/04853 A1 | 2/2000 |

OTHER PUBLICATIONS

Examination Report for EP 99928410.2, EP Regional Phase of PCT/US99/12622, mailed May 12, 2004.

International Search Report and Written Opinion for PCT/US2010/001139, mailed Jul. 21, 2010.

CareDrape® Cardiac Warming Blanket, Dec. 16, 2009 http://www.nellcor.com/prod/Product.aspx?S1=TMP&S2=id=253.

Abstract of DE3320771, Dec. 13, 1984, EPO, Noack.

* cited by examiner

INFLATABLE CONVECTIVE PAD FOR SURGERY

PRIORITY

This patent application is a divisional of U.S. patent application Ser. No. 10/935,992, filed Aug. 8, 2004.

BACKGROUND

The field concerns an inflatable convective pad is adapted to be deployed under a person in connection with surgery.

Warming a person during surgery affords clinical benefits, including prevention or treatment of hypothermia, encouragement of immune system function, and promotion of wound healing. An inflatable blanket is used to warm a person perioperatively. Such a blanket, when inflated with heated air, warms the person principally by convection of warmed air through the blanket, although conduction and radiation of heat from the blanket also contribute to warming.

However, blanketing a person for warming may interfere with particular surgical procedures. For example, during cardiac surgery access to the thorax, groin and extremities is necessary when blood vessels must be harvested from the legs and arms for bypass construction on the heart. Deploying an inflatable blanket over a person may interfere with if not prevent the necessary access. Adapting the blanket to avoid interference by reducing its size may compromise its capacity to warm the person. Adapting the blanket to provide access by separable seals may extend and complicate the surgery due to need to integrate the operation and management of the blanket with surgical protocols.

One way to achieve the benefits of warming a person during cardiac surgery without the interference caused by a blanket is to utilize an inflatable convective pad which may be disposed beneath the person. The person is laid on the pad and the pad warms the person by convection of warmed air, and also by conduction and radiation, from beneath and around the person while leaving the chest and periphery uncovered. An inflatable convective pad is described in the assignee's U.S. Pat. No. 6,102,936. The assignee's Model 555 pediatric underbody blanket is another example of an inflatable convective pad. However, in spite of the access to necessary surgical sites that is available with an inflatable convective pad, there are drawbacks to its use in certain surgeries.

For example, in cardiac surgery the widely used "draw sheet" protocol interferes with effective operation of an inflatable convective pad. In this regard, in preparation for surgery, a sheet of material (called a "draw sheet"), typically between two and three feet in width and four to six feet in length, is centered transversely under a person and each end of the sheet is threaded between one arm and the adjacent side of the person. Each end is then brought over the bicep and dropped along the outside of its respective arm, tightened over the arm, and then pinned between the operating table mattress and the operating table. The draw sheet retains or immobilizes the arms against movement during surgery. When an inflatable convective pad is deployed for warming, the draw sheet itself, and the immobilized arms, press against the sides of the pad and restrict airflow through the device.

Also, many thoracic surgeries are performed on ischemic patients with impaired circulation to extremities. Feet especially exhibit the effects of low oxygen saturation in tissue resulting from poor blood flow. This condition is ischemia. Ischemic extremities are particularly vulnerable to injury from the combination of heat and pressure, and burns can result where feet press against an inflatable convective pad inflated with heated, pressurized air.

SUMMARY

These and other problems are solved in an inflatable convective pad having at least two openings, each located in an area of the pad between two ends of the pad and between a respective side and the center of the pad. The openings provide for restraint of the person's arms during surgery. Heat transfer to the person's feet is reduced through an area near one end of the pad by blocking or preventing convective heat transfer in that area.

SPECIFICATION

An inflatable convective pad (also called simply a "pad" in this specification) has two ends, two sides, and a pneumatic structure. At least one inlet port in the pad opens into the pneumatic structure. The pad is inflatable. That is to say, the pad, flaccid when not in use, tautens when a stream of pressurized air is received in the pneumatic structure by way of an inlet port. The pad has a surface to support a person. That surface, at least, is permeable to air. When a stream of warmed pressurized air is received in the pneumatic structure, the pad inflates and warmed air circulates from the pneumatic structure, through the surface, to warm the person.

An inflatable convective pad shown in these figures and described in this specification may be constructed using techniques and materials which are known in the art, or which are equivalent thereto. The specific details of construction and materials that are set forth in this specification are meant for illustration only. Generally, the construction and materials with which an inflatable convective pad may be made include two or more sheets of flexible material that are brought together and bonded, joined, or sealed at a periphery, and at multiple points within the periphery. This pad may be made, for example, in a continuous manufacturing process which joins multiple webs of material. Other construction methods may also be employed.

The two or more sheets of flexible permeable material are joined to form a pneumatic structure having at least one surface through which pressurized air that inflates the structure circulates, passes, or exits toward the body of a person laid on the surface. One or more inlet ports, with provision for retention of an air hose nozzle, are provided for admitting a stream of warmed, pressurized air into the pneumatic structure, from an air hose connected to a heater/blower unit. The warmed air circulating through the surface causes the person to be warmed. Although convection is the principal mode of warming, the structure itself, when inflated with warmed air, radiates heat as well. Further, where the structure contacts the person's body, heat may, also be transferred by conduction.

The sheets of material of which a pad is formed may be made of synthetic or natural materials, or a natural/synthetic blend. The sheets are made, or processed, to be permeable to air. One possible construction for the inflatable thermal pad is described in the referenced U.S. Pat. No. 6,102,936 at column 5, line 28 through column 6, line 7. A pad so constructed is illustrated in FIG. 1.

Figure 1:
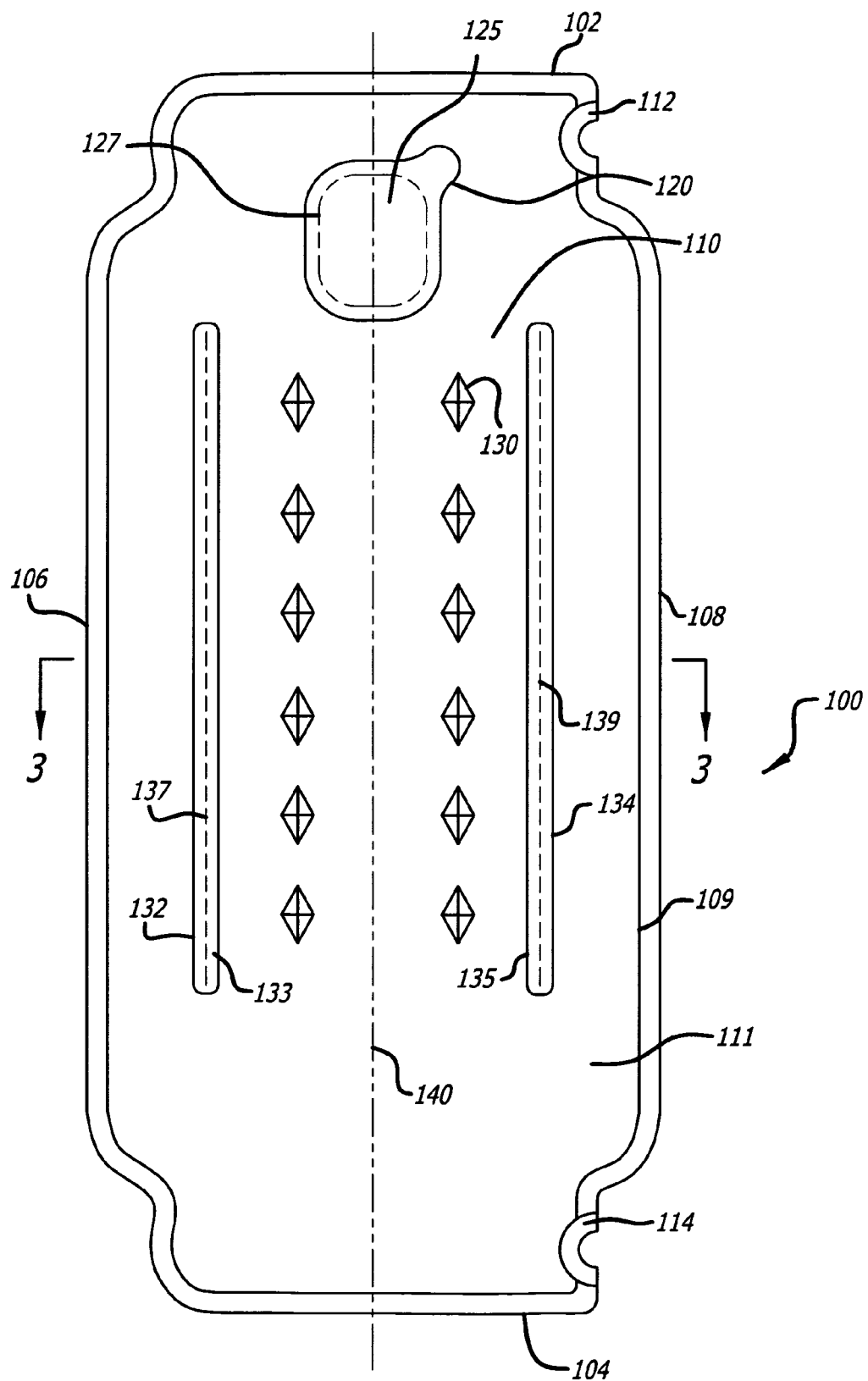
FIG. 1 is a plan view of an inflatable convective pad.

The inflatable convective pad 100 of FIG. 1 is seen in plan view, looking toward an upper surface 110 of the pad 100. The pad 100 has a head end 102, a foot end 104, and two sides 106 and 108. The upper surface 110 is permeable and active, with exceptions to be described. The pad may be constructed as described above from sheets sealed together by a seal 109 extending around the periphery of the pad. At least one inlet port is provided to admit a stream of warmed pressurized air into the pneumatic structure of the pad 100. For example two inlet ports 112 and 114 are disposed at each end of the pad 100. The inlet ports 112 and 114 may be constructed and selectively operated with plugs as taught in the assignee's U.S. Pat. No. 5,997,572. So constructed, an inlet port is constituted of a collar of relatively stiff material such as cardboard that surrounds an opening into the pneumatic space of the pad 100. The collar receives and retains the nozzle of an air hose while the air hose delivers a stream of warmed pressurized air into the pneumatic space. If not used, the collar is closed by a removable plug. Alternatively, the inlet ports may be sleeves of material with means to retain the nozzle of an air hose.

The sheets of which the inflatable convective pad 100 is made are sealed together at locations within the seal 109 around the periphery of the pad 100. At one location, near the head end 102, a continuous closed seal 120 between the sheets defines an uninflatable area 125 that is closed off from the pneumatic structure and is therefore inactive. The pattern of the seal 120 incorporates a protrusion from the elliptical outline. This protrusion is intended to provide air flow between the sides 108 and 106. A line of weakness or perforation 127 permits a portion of the uninflatable area 125 to be separated and removed from the pad 100. The sheets are also sealed together at other locations 130 within the periphery to control the size, shape, and operation of the pad when inflated. Some of these locations 130 may include drain passages to draw off fluids from the surface 110 that may accumulate before, during and/or after surgery. Drain passages may be constructed as taught in the referenced U.S. Pat. No. 6,102,936.

As will be described in more detail below, the portion of the pad 100 within the seal pattern 120 is where a person's head may be received while the portion 111 near the foot end 104 is where a person's feet may be supported.

In at least two further locations in the inflatable convective pad 100, openings through the pad are defined. For example, two laterally-aligned, spaced-apart openings through the pad 100 may be provided, each of enough size and located appropriately to receive a draw sheet or equivalent retainer and/or an arm of a person. For ease of explanation, such openings are illustrated and described as "slits" in this specification, with the understanding that the precise configuration will be a matter of design choice and that many equivalents of the slits may be realized in an inflatable convective pad. Thus, in order to define at least two openings through the pad 100 through which retainers or limbs may be threaded, continuous closed seals 132 and 134 between the sheets establish elongate uninflatable areas 133 and 135 within which are formed slits 137 and 139 that open through the pad 100. The slits 137 and 139 may be formed when the pad 100 is constructed. Or, elongate lines of weakness or perforations may be formed in the uninflatable areas 133 and 135 so that either or both slits may be selectively opened when the pad 100 is put to use.

As seen in FIG. 1, the slit 137 is located between the two ends 102 and 104 of the pad 100 and between the side 106 and central axis 140 of the pad 100. The slit 139 is located between the two ends 102 and 104 of the pad 100 and between the side 108 and central axis 140 of the pad 100. Preferably, but not necessarily, the slits 137 and 139 are oriented to be generally parallel to each other, the side 106 and 108, and the central axis 140. In addition, the elongate configuration of the slits 137 and 139 is by no means the only shape or outline contemplated for these elements.

Figure 2:
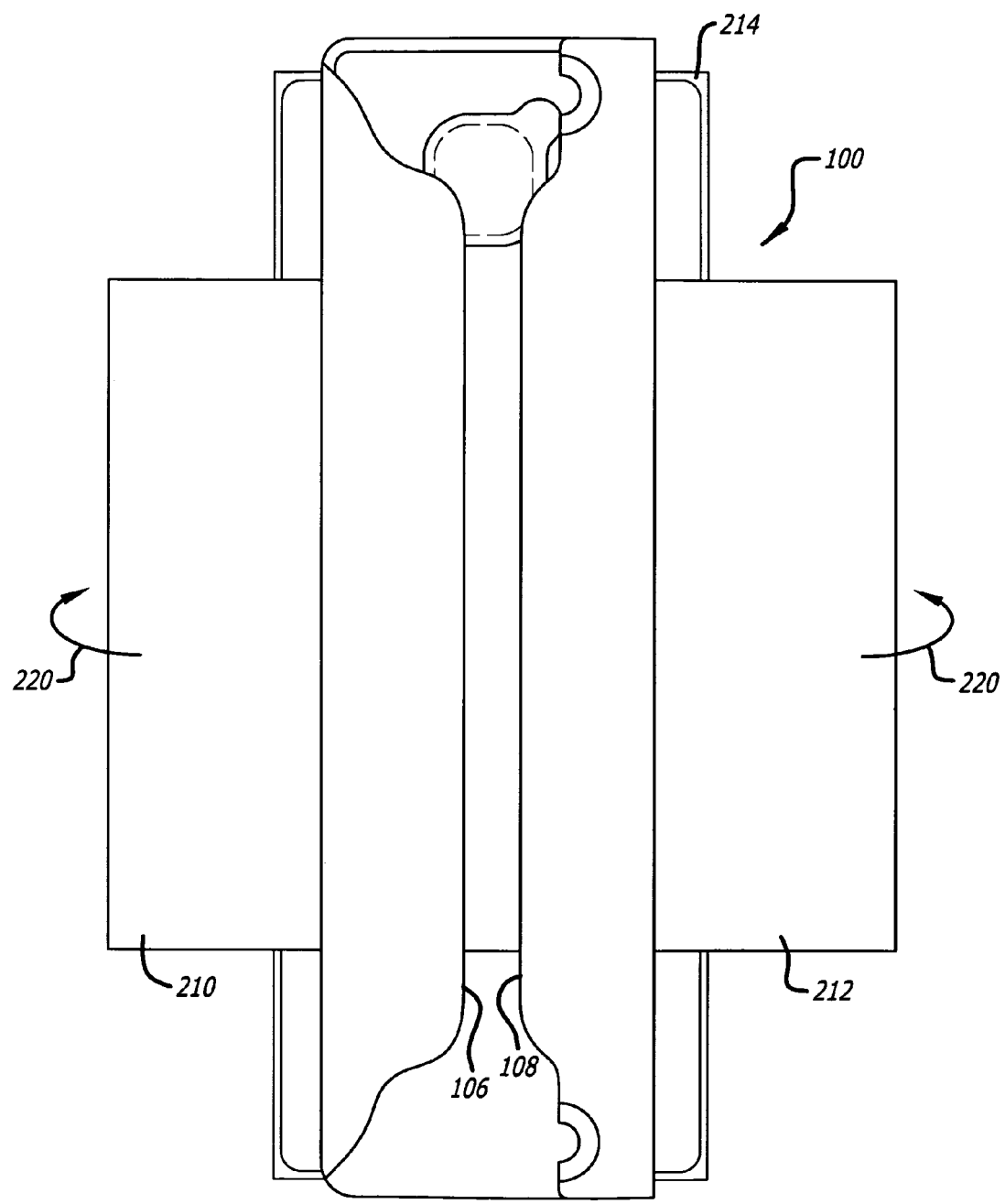
FIG. 2 is a plan view of the inflatable convective pad of FIG. 1 with side portions folded to show optional features.

FIG. 2 shows the inflatable convective pad 100, with the sides 106 and 108 folded over the upper surface 110 to reveal optional retaining flaps 210 and 212 that may be formed integrally with or attached to the pad 100 underneath the sides 106 and 108. For example, these retaining flaps 210 and 212 may be incorporated into the construction of the pad 100 in the manner taught in the referenced U.S. Pat. No. 6,102,936 at column 6, lines 8-30. When the pad 100 is deployed for use these retaining flaps are folded in the direction of the arrows 220 toward and around a mattress 214 on which the pad 100 rests.

Figure 3A:
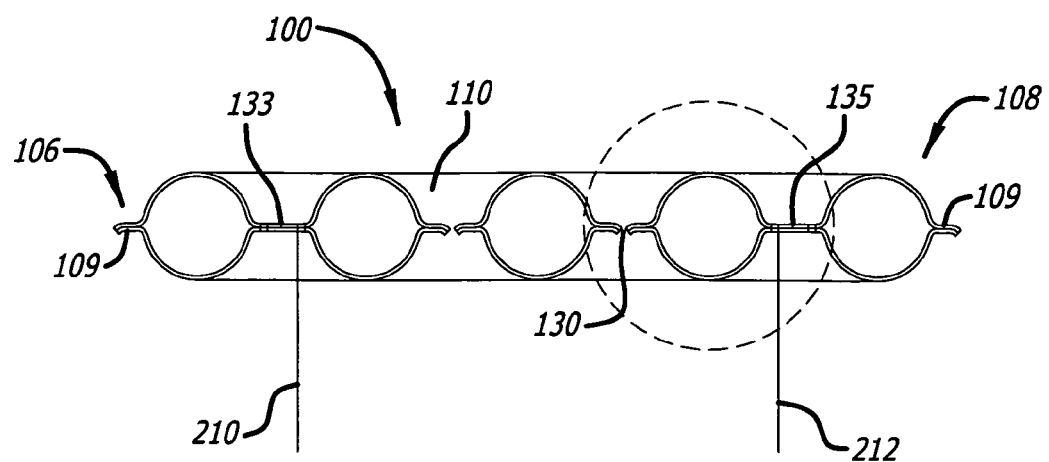
FIG. 3A is a side sectional view of the inflatable convective pad of FIG. 1, when inflated
Figure 3B:
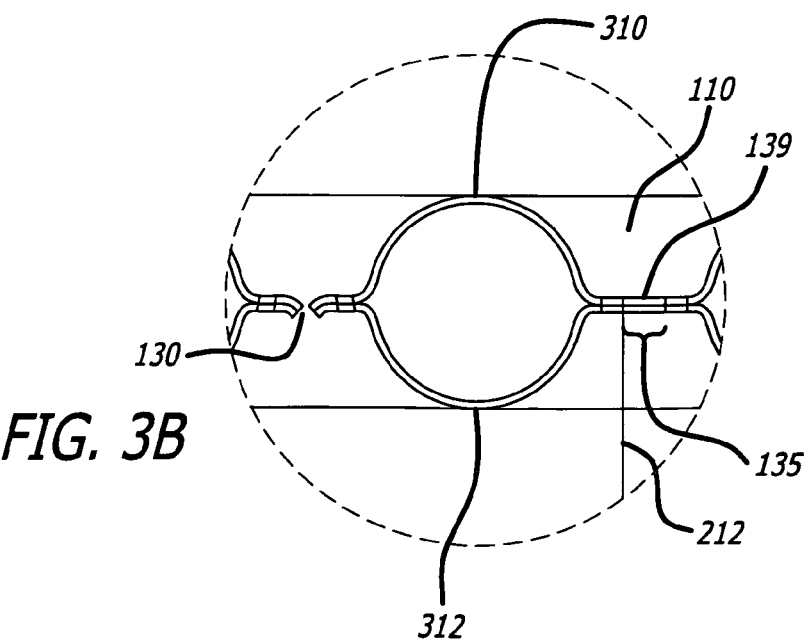
FIG. 3B is a magnified portion of the inflatable convective pad shown in FIG. 3A.

FIG. 3A is a sectional view of the inflatable convective pad 100 taken along the lines 3-3 of FIG. 1 with the pad 100 inflated. FIG. 3B is a magnified portion of FIG. 3A. The multiple sheet construction is illustrated in these figures. An air-permeable sheet ("permeable sheet") 310 is joined to a sheet 312 which may also be permeable if the pad 100 is to be reversible. The surface 110 is the upper or outer surface of the permeable sheet 310. The seal 109 bonds or joins the sheets 310 and 312 to form a pneumatic structure with space 313 to receive and distribute warmed pressurized air introduced through an inlet port. The warmed pressurized air causes the pad 100 to inflate. When inflated, the pad 100 operates by circulating warmed pressurized air through at least the surface 110. FIG. 3B shows a drain passage at a seal location 130 and the perforation or line of weakness defining the slit 139 in the elongate uninflatable area 135 near the side 108 of the pad 100.

Figure 4:
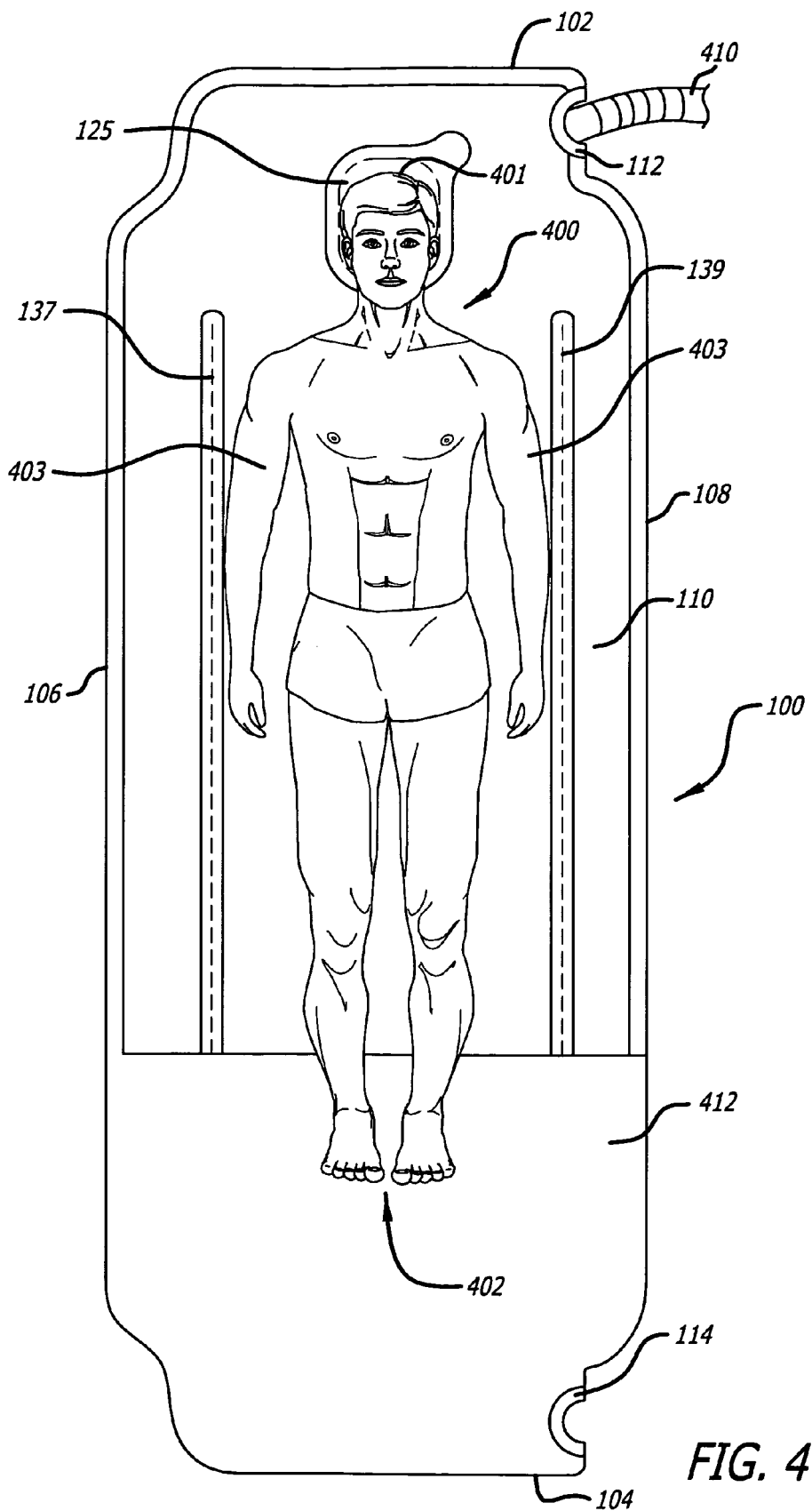
FIG. 4 is a plan view of the inflatable convective pad of FIG. 1 with a person supported thereon.

FIG. 4 shows a person 400 lying on the surface 110 with the person's head 401 positioned in the uninflatable area 125 and the person's feet 402 disposed on the near the foot end 104 of the inflatable convective pad 100. The nozzle of an air hose 410 is received in the inlet port 112, while the inlet port 114 is plugged. The pad 100 is inflated by a stream of warmed pressurized air flowing through the air hose 410 into the pneumatic structure of the pad. The warmed pressurized air inflates the pad 100 and the person 400 is warmed by air which circulates from the pneumatic structure through the surface 110. To prevent or mitigate thermal injury to the person's feet 402, the area 111 of the surface 110 near the foot end 104 is inactive. The area 111 may be rendered inactive in ways described above. In the example shown in FIG. 4, a sheet 412 of non-permeable material covering the surface portion 111 is incorporated into the structure of the pad 100 overlying the sheet 310 near the foot end 104. This blocks air from circulating to the person's feet 402, and reduces heat transfer to the feet from the pad 100. As FIG. 4 suggests, the pad 100 is sized such that the slits 137/139 are positioned near the person's arms 403 when the arms are drawn in to extend along the sides of the person. For example, the pad 100 may be sized to locate the slits outside of the person's arms, that is to say between the person's arms 403 and the sides 106 and 108 of the pad 100.

Figure 5A:
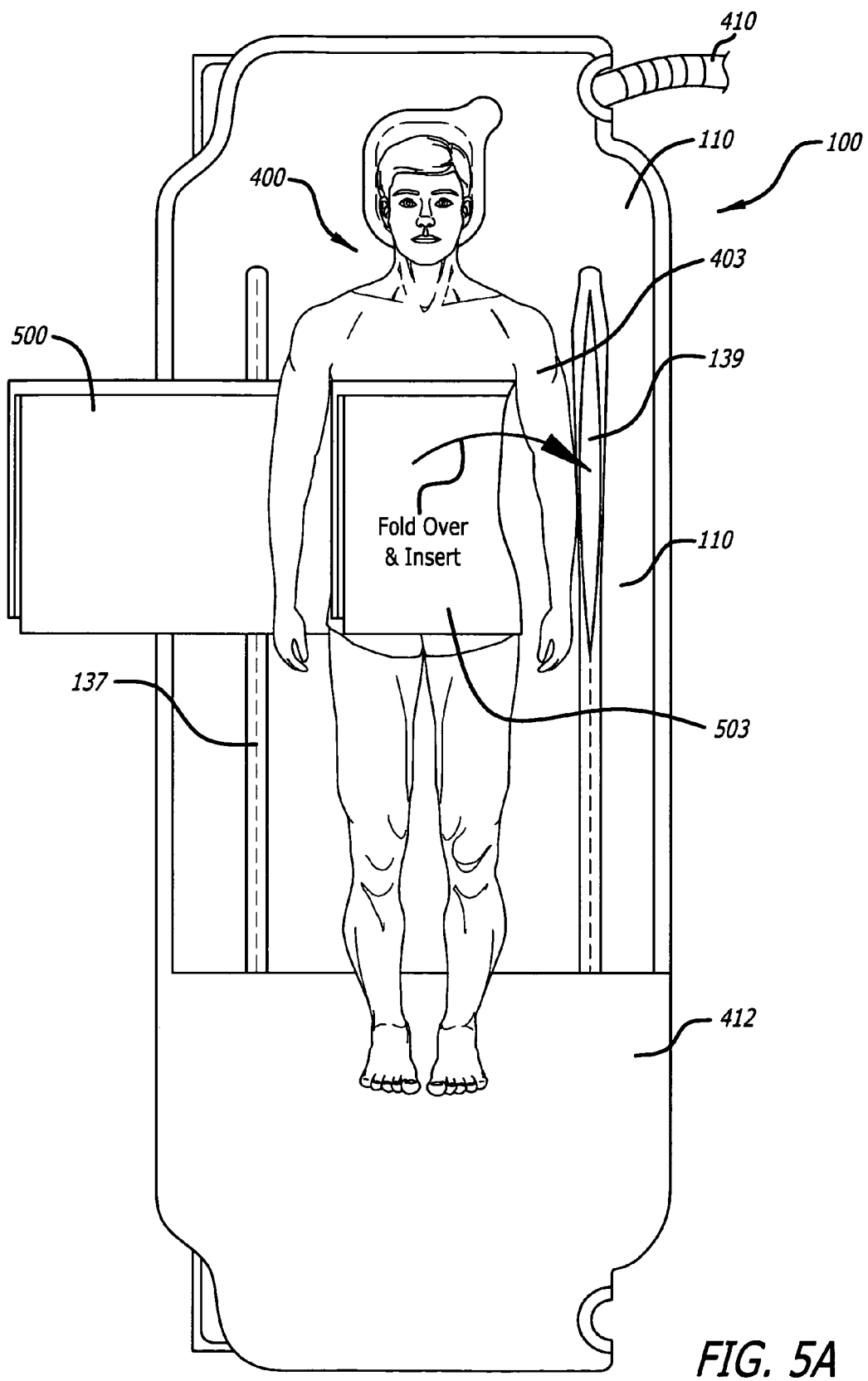
FIG. 5A is a plan view of the inflatable convective pad of FIG. 1, with a person supported thereon and a limb retainer partially threaded thereto.
Figure 5B:
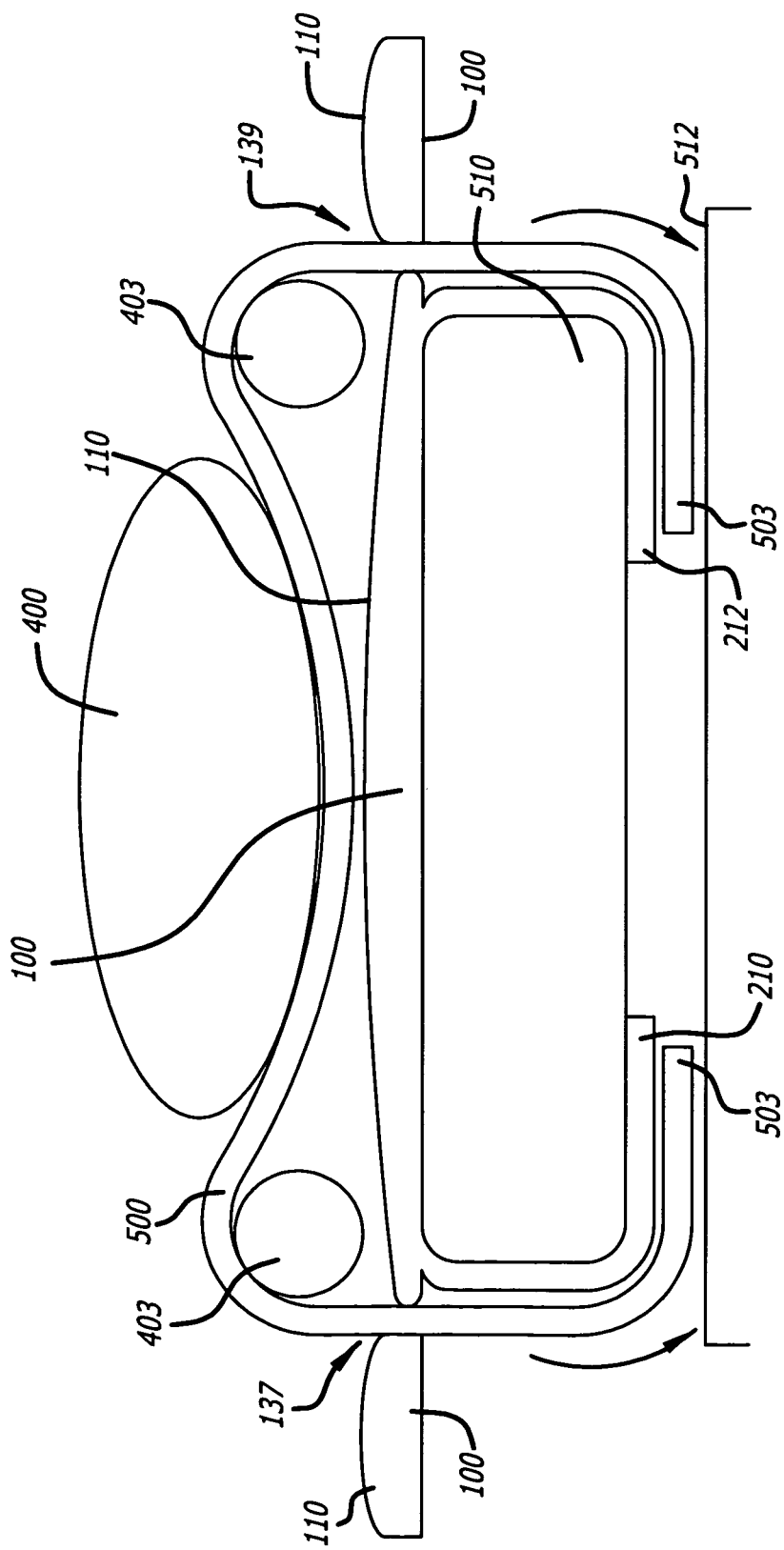
FIG. 5B is a schematic cross section of the inflatable convective pad of FIG. 5A, with a person supported thereon and a limb retainer fully threaded thereto.
Figure 5C:
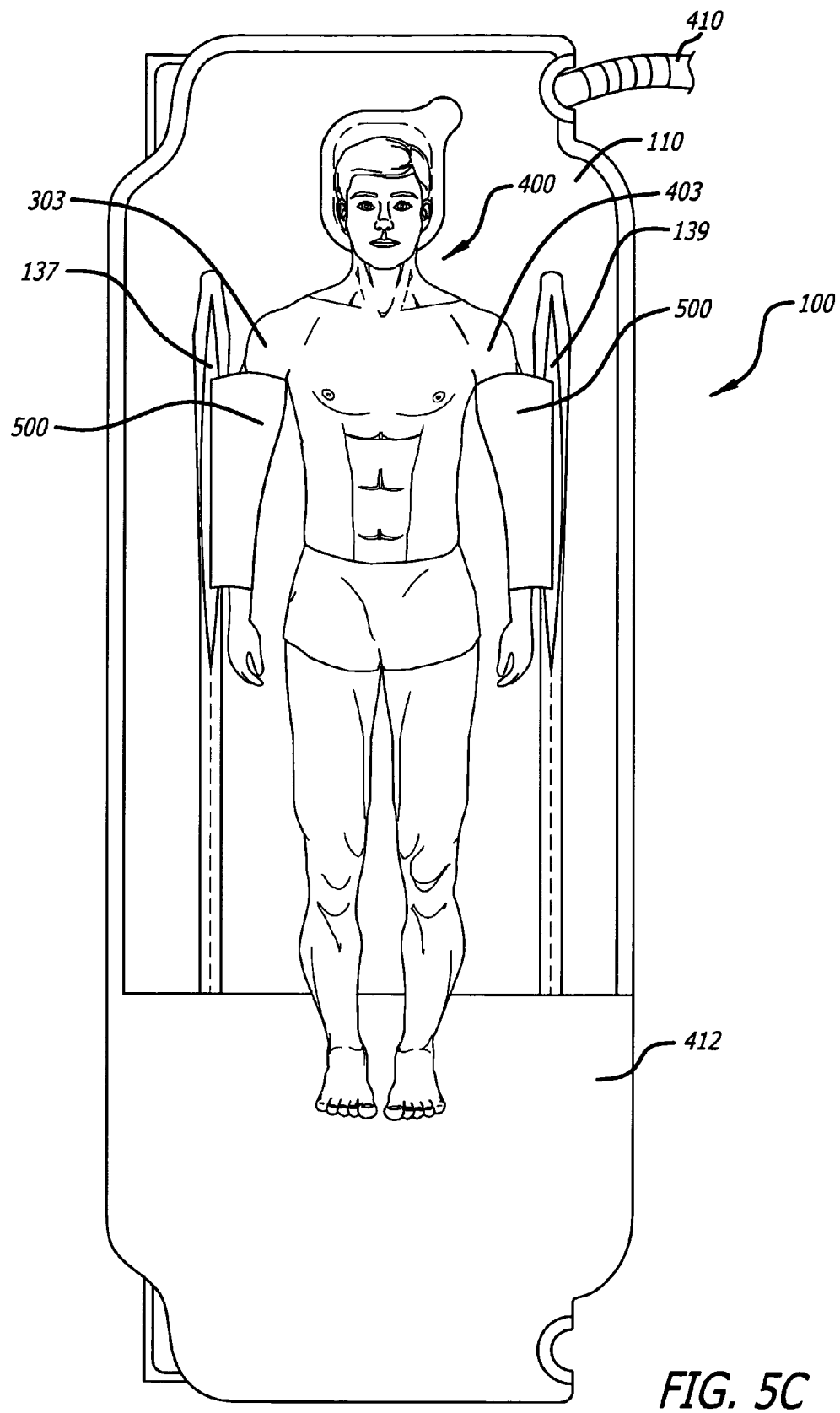
FIG. 5C is a plan view of the inflatable convective pad of FIG. 5A, with a person supported thereon and a limb retainer fully threaded thereto.

FIGS. 5A-5C illustrate one use of the slits 137 and 139 to restrain the person's arms 403 during surgery when the inflatable convective pad 100 is deployed on an operating table and inflated with warmed pressurized air, and the person 400 is supported on the surface 110 of the pad 100. In this regard, if not already open, the slits 137 and 139 are opened by tearing along the lines of weakness or perforations. Then a draw sheet 500 is centered transversely under the person 400 and each end 503 of the draw sheet 500 is threaded upwardly between one of the person's arms 403 and the adjacent side of the person 400. Each end 503 is then folded over a respective arm 403 at the bicep, dropped along the outside of the respective arm, tightened over the arm, and then inserted into the adjacent slit 137/139. As best seen in FIG. 5B, the ends 503 of the draw sheet 500 are folded around the sides of and under an operating table mattress 510 and pinned between the mattress 510 and an operating table 512. FIG. 5B also shows the optional retaining flaps 210 and 212. If provided, the retaining flaps 210 and 212 are folded around the sides of and under the operating table mattress 510 before the ends 503 of the draw sheet 500 and are pinned between the mattress 510 and the ends 503 of the draw sheet 500. As clearly seen in FIG. 5C, during surgery the person 400 is received on the permeable surface 110 and the person's arms 403 are restrained by the draw sheet 500 that has been threaded through the slits 137/139 and retained beneath the pad 100. The person 400 is warmed during surgery by convection of warmed air through the surface 110.

Figure 6:
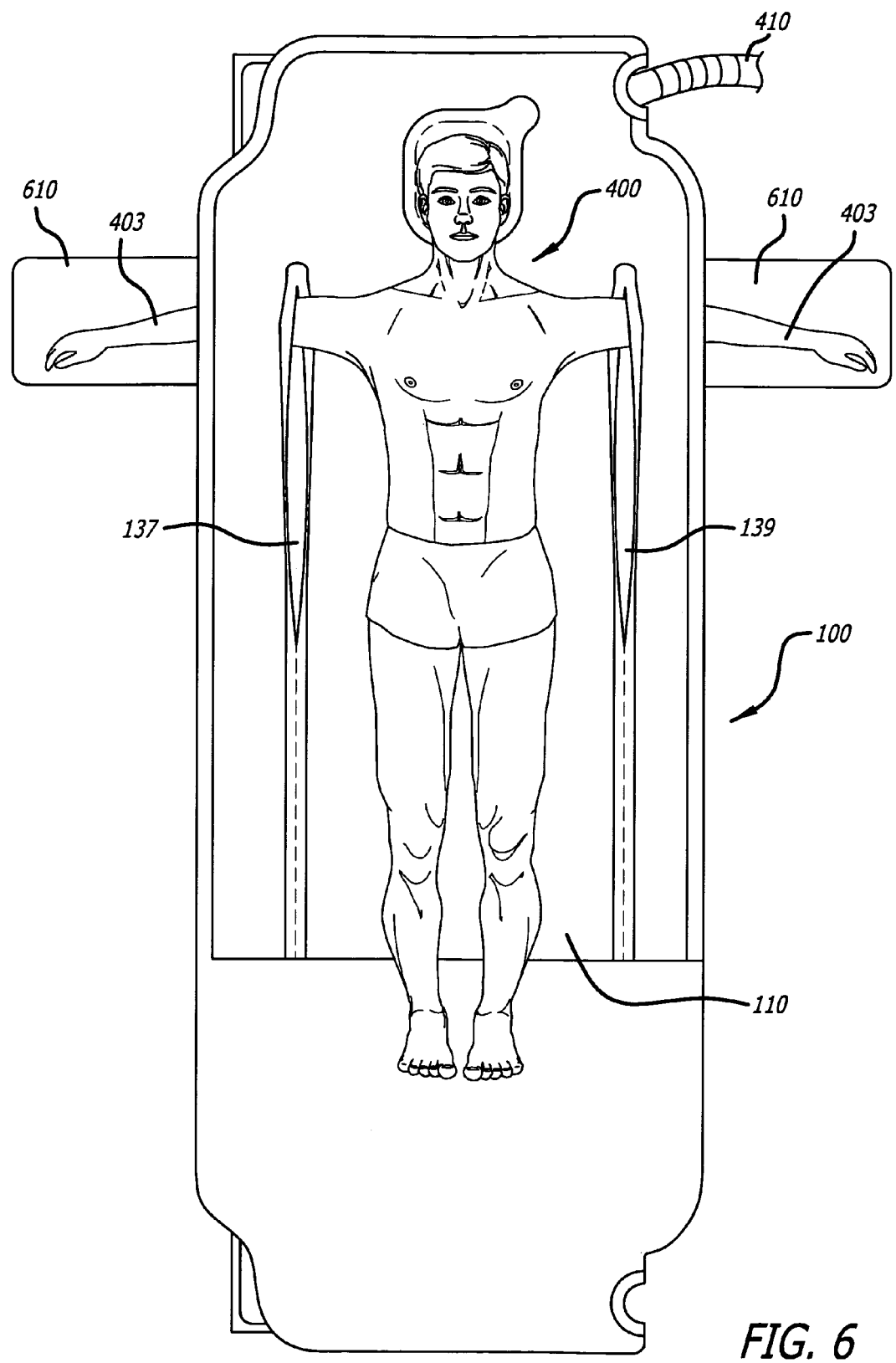
FIG. 6 is a plan view of the inflatable convective pad of FIG. 1, with a person supported thereon in a first position with arms extended and threaded through the pad.
Figure 7:
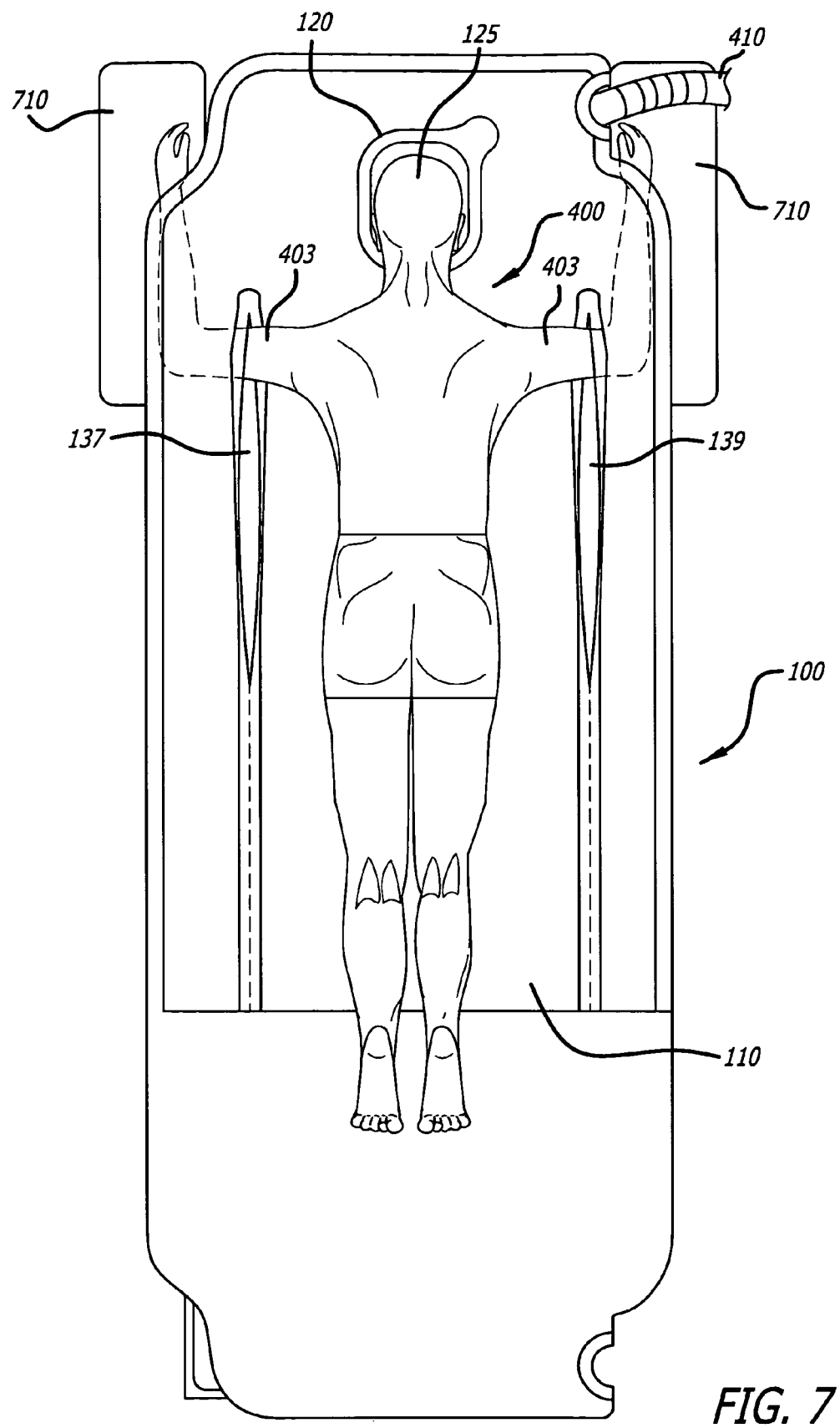
FIG. 7 is a plan view of the inflatable convective pad of FIG. 1, with a person supported thereon in a second position with arms partially flexed and threaded through the pad.
Figure 8:
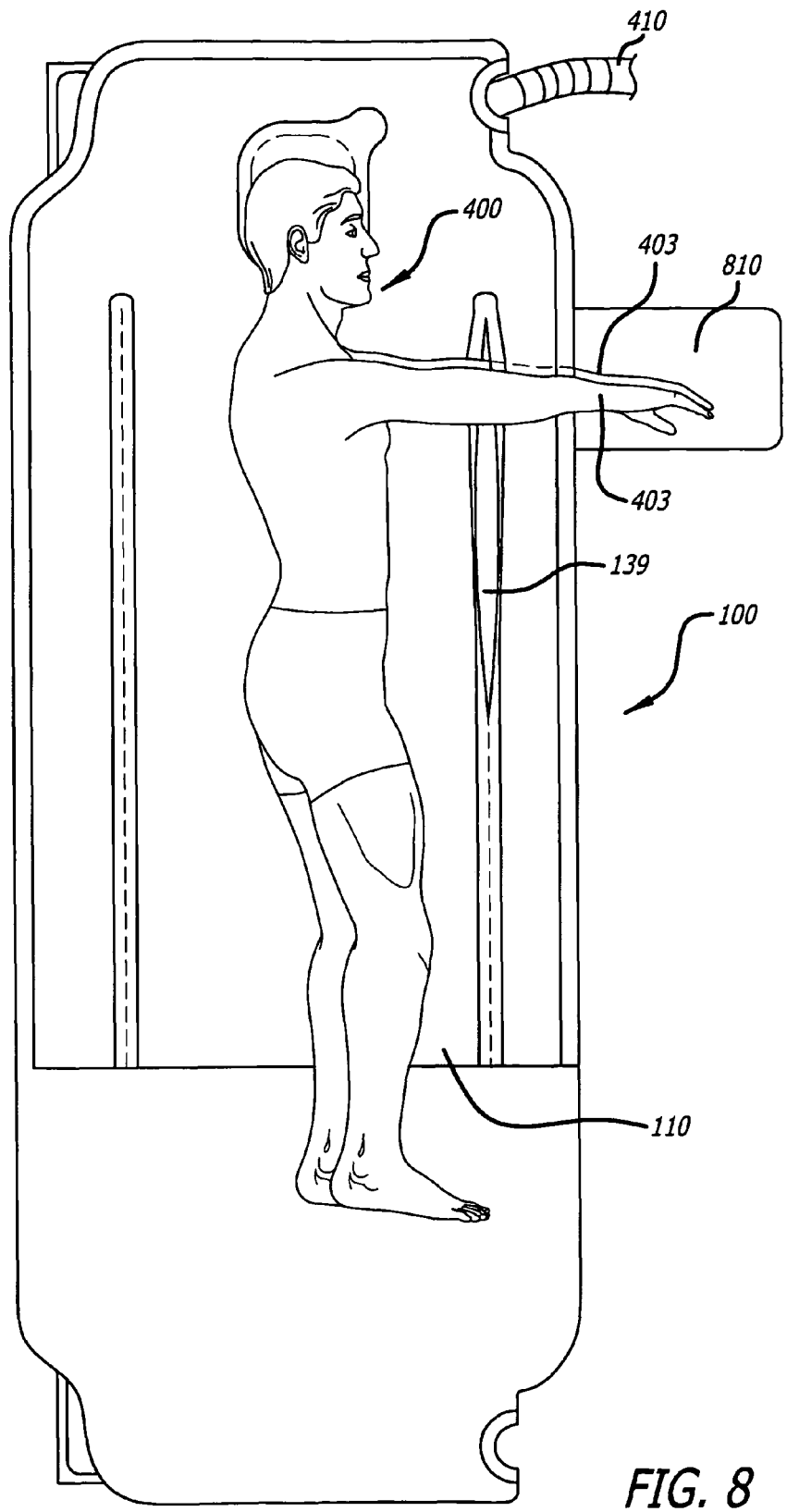
FIG. 8 is a plan view of the inflatable convective pad of FIG. 1, with a person supported thereon in a third position with arms extended and one arm threaded through the pad.

The inflatable convective pad 100 with slits 137/139 may also be used to pass a limb of a person through the pad during surgery. Various examples in this regard are illustrated in FIGS. 6, 7, and 8. In FIG. 6, the pad 100 is disposed on a cruciform operating table with a transverse piece 610. The person 400 is received face up on the permeable surface 110 with arms 403 outstretched in opposing directions. Each arm is received in and threaded through a respective slit 137/139 to be positioned between the pad 100 and the transverse piece 610. In FIG. 7, the pad 100 is disposed on an operating table with lateral arm rests 710. The person 400 is received face down on the permeable surface 110 with arms 403 extended outwardly to the elbows and then upwardly from the elbows to the hands. In this position, the uninflatable area 125 within the seal 120 is removed to permit the person 400 to breathe freely, to accommodate a breathing apparatus or other medical instrument, or to visualize the person. Each arm 403 is received in and threaded through a respective slit 137/139 to be restrained between the pad 100 and a respective one of the arm rests 710. In FIG. 8, the pad 100 is disposed on an operating table with one transverse piece 810. The person 400 is received on his side on the permeable surface 110 with both arms 403 outstretched in the same direction. One arm 403 is received in and threaded through the slit 139 to be positioned between the pad 100 and the transverse piece 810. The other arm 403 is laid across the surface 110 atop the lower arm.

An inflatable convective pad for supporting and warming a person and having at least two openings for retaining one or more limbs of a person during surgery has been described and illustrated. The various embodiments of the pad that are shown and specified are meant to serve as examples of underlying principles, and many other equivalent embodiments will be evident to those of ordinary skill. The scope of patent protection for such a device is limited only by the claims below.

We claim:

1. A method of using an inflatable convective pad, comprising:
    inflating the pad with warmed pressurized air;
    convecting warmed air through a surface of the pad;
    supporting a person on the surface; and,
    threading a retainer around the person's arms and through the pad;
    wherein the retainer comprises a draw sheet, the pad includes spaced-apart openings through the pad, and threading includes:
    positioning the draw sheet between the person and the surface;
    threading each end of the draw sheet between one of the person's arms and an adjacent side of the person;
    folding each end of the draw sheet over a respective arm;
    inserting each end of the draw sheet through an opening through the pad; and
    securing each end of the draw sheet beneath the pad.

2. The method of claim 1, wherein the pad is disposed on an operating table mattress, further including folding the ends of the draw sheet around the sides of and under the operating table mattress.

3. The method of claim 1, wherein the pad is disposed on an operating table mattress and includes retaining flaps, further including folding the retaining flaps around the sides of and under the operating table mattress.

4. The method of claim 3, further-including folding the ends of the draw sheet around the sides of and under the operating table mattress following folding the flaps.

* * * * *

UNITED STATES PATENT AND TRADEMARK OFFICE
CERTIFICATE OF CORRECTION

| | | |
|---|---|---|
| PATENT NO. | : 8,460,354 B2 | Page 1 of 1 |
| APPLICATION NO. | : 12/925249 | |
| DATED | : June 11, 2013 | |
| INVENTOR(S) | : Anderson et al. | |

It is certified that error appears in the above-identified patent and that said Letters Patent is hereby corrected as shown below:

In the Specification

Column 1
Line 7; Delete "Aug. 8, 2004." and insert -- Sep. 8, 2004. --, therefor.

Signed and Sealed this
Twenty-second Day of October, 2013

Teresa Stanek Rea
*Deputy Director of the United States Patent and Trademark Office*